United States Patent
Zhdaneev (10) Patent No.: US 7,781,737 B2
(45) Date of Patent: Aug. 24, 2010

(54) APPARATUS AND METHODS FOR OIL-WATER-GAS ANALYSIS USING TERAHERTZ RADIATION

(75) Inventor: Oleg Zhdaneev, Cambridge, MA (US)

(73) Assignee: Schlumberger Technology Corporation, Cambridge, MA (US)

( * ) Notice: Subject to any disclaimer, the term of this patent is extended or adjusted under 35 U.S.C. 154(b) by 0 days.

(21) Appl. No.: 11/613,675

(22) Filed: Dec. 20, 2006

(65) Prior Publication Data

US 2008/0149819 A1   Jun. 26, 2008

(51) Int. Cl.
    G01J 5/02       (2006.01)
(52) U.S. Cl. .............................................. 250/339.08
(58) Field of Classification Search .............................
                                              250/339.01–339.15
    See application file for complete search history.

(56) References Cited

U.S. PATENT DOCUMENTS

| | | | |
|---|---|---|---|
| 5,166,747 | A | 11/1992 | Schroeder et al. |
| 5,331,409 | A * | 7/1994 | Thurtell et al. ............... 356/437 |
| 6,075,611 | A * | 6/2000 | Dussan et al. ................ 356/432 |
| 6,218,662 | B1 * | 4/2001 | Tchakarov et al. ........... 250/256 |
| 6,420,708 | B2 * | 7/2002 | Wilks et al. .............. 250/339.07 |
| 6,723,991 | B1 * | 4/2004 | Sucha et al. ............. 250/341.1 |
| 6,849,852 | B2 | 2/2005 | Williamson |
| 7,315,175 | B2 | 1/2008 | Cole |
| 2002/0043620 | A1 * | 4/2002 | Tchakarov et al. ......... 250/269.1 |
| 2002/0139929 | A1 * | 10/2002 | Mullins et al. .............. 250/255 |
| 2002/0169345 | A1 | 11/2002 | Johnson |
| 2003/0035205 | A1 | 2/2003 | Zisk, Jr. |
| 2003/0226961 | A1 * | 12/2003 | Hagmann .................... 250/234 |
| 2004/0129874 | A1 | 7/2004 | Torgersen et al. |
| 2004/0219064 | A1 | 11/2004 | Raghuraman et al. |
| 2004/0258343 | A1 * | 12/2004 | Burge .......................... 385/12 |
| 2005/0007583 | A1 * | 1/2005 | DiFoggio ..................... 356/301 |
| 2005/0037384 | A1 * | 2/2005 | Braig et al. ..................... 435/6 |

(Continued)

FOREIGN PATENT DOCUMENTS

WO       2004048969 A1    6/2004

OTHER PUBLICATIONS

Pedersen et al., "THz Time-Domain Spectroscopy of Nonpolar Liquids,", 1992, IEEE Journal of Quantum Electronics, vol. 28, No. 10, pp. 2518-2522.*

(Continued)

*Primary Examiner*—David P Porta
*Assistant Examiner*—Kiho Kim
(74) *Attorney, Agent, or Firm*—James McAleenan; Vincent Loccisano; Brigid Laffey (57) ABSTRACT

Methods and apparatus for analyzing gas-oil-water compounds in oilfield and other applications are disclosed using terahertz radiation. A sample analyzer includes a sample chamber having a fluid communication port configured to receive the sample. The analyzer also includes a filter to filter samples and selectively remove oil, water or gas from reservoir mixture received by the sample chamber. A terahertz (THz) radiation detector is provided in electromagnetic communication with the sample. The terahertz detector provides a detected output signal indicative of the terahertz electromagnetic radiation detected from the sample. In some embodiments, the device also includes a terahertz source illuminating the sample, the terahertz detector detecting a portion of the terahertz source illumination as modified by the sample. The detected portion of the spectrum of terahertz radiation can be processed to analyze the composition of the sample.

29 Claims, 9 Drawing Sheets

U.S. PATENT DOCUMENTS

| | | |
|---|---|---|
| 2005/0099618 A1* | 5/2005 | DiFoggio et al. ............... 356/70 |
| 2005/0111129 A1* | 5/2005 | Crawford et al. ............... 360/68 |
| 2006/0043298 A1 | 3/2006 | Kawase et al. |
| 2006/0049356 A1 | 3/2006 | Shen et al. |
| 2006/0054824 A1 | 3/2006 | Federici et al. |
| 2006/0055476 A1 | 3/2006 | Kazakov et al. |
| 2006/0056586 A1 | 3/2006 | Uetake et al. |
| 2006/0076518 A1 | 4/2006 | Barker et al. |
| 2006/0163467 A1 | 7/2006 | Raghuraman et al. |
| 2006/0165344 A1 | 7/2006 | Mendez et al. |
| 2007/0131018 A1* | 6/2007 | Alspach et al. ............... 73/1.16 |

OTHER PUBLICATIONS

Sherwin et al., "Oppertunities in THz Science", Report of a DOE-NSF-NIH Workshop held Feb. 12-14, 2004, Arlington, VA.

Grob et al., "Modern Practice of Gas Chromatography", Chapter Six, Detectors in Modern Gas Chromatography, Luis A. Colon and Lisa J. Baird, pp. 277-337.

Taday et al., "Technological advances in terahertz pulsed systems bring far-infrared spectroscopy into the spotlight", SpectroscopyEurope, pp. 20-24, 2004.

Mueller, "Terahertz Radiation: Applications and Sources," The Industrial Physicist, pp. 27-29, Aug./Sep. 2003.

* cited by examiner

APPARATUS AND METHODS FOR OIL-WATER-GAS ANALYSIS USING TERAHERTZ RADIATION

FIELD OF THE INVENTION

The present invention relates generally to material composition analysis. More specifically, the present invention relates to oil-water-gas analysis using a radiation detection and analysis system operating in a terahertz region of the electromagnetic spectrum.

BACKGROUND OF THE INVENTION

Precise and real-time identification of reservoir fluid composition are important for successful evaluation and development of oil-gas-water reservoirs. Reservoir fluid composition influences all aspects of reservoir development including well design, method to improve recovery factor, and production strategy. It is important to evaluate reservoir fluid compositions in real time, or at least near real time. Real-time analysis preferably includes evaluations within the well bore, also referred to as "downhole." It is usually possible, although typically less timely, to evaluate extracted samples in a surface laboratory. To obtain downhole samples, a special tool is lowered into the well and set across points of interest. An example of such a tool is described in U.S. Pat. No. 5,166,747, assigned to Schlumberger Technology Corporation, the disclosure of which is incorporated herein by reference in its entirety. By establishing communication with the reservoir, the reservoir fluids are extracted, or withdrawn from the reservoir towards the tool. The extracted fluids are directed into fluid storage and fluid composition analysis modules.

Methods exist for determining fluid composition. These methods typically include a detection device capable of performing gas and liquid chromatography. Such devices can qualitatively and/or quantitatively respond to analyzable mixtures, including hydrocarbon mixtures encountered in oilfield applications. Some of the most commonly used detectors include thermal conductivity detectors, flame ionization detectors, photometric detectors, and photo ionization detectors.

Techniques exist for determining fluid composition, which inject infrared light into a flowing sample and measure a portion of the injected light to determine an amount of absorption by the sample. These techniques use optical or infrared (IR) absorption detectors to detect the difference in beam intensity before and after its passing through a sample cell, which includes a sample mixture to be analyzed. Atoms and/or molecules within the sample capture some of the photons as they traverse the sample cell through a process referred to as electron excitation—the movement of an electron within an atom or molecule of the sample to a higher energy state. Such techniques generally determine electron excitation of molecules within the sample. Unfortunately, it is often difficult and at times impossible to select wavelengths from within the optical band that will provide substance identification due to overlapping absorption peaks or emission peaks that occur within this range.

SUMMARY OF THE INVENTION it is an object of the invention to provide a solution for determining composition of a fluid sample without suffering from overlapping absorption peaks that occur within the optical and IR spectral range.

Fortunately, problems associated with overlapping peaks within the absorption or emission spectra can be substantially eliminated by using electromagnetic radiation selected from the terahertz (THz) region of the electromagnetic spectrum. This generally includes electromagnetic radiation having wavelengths between about 3 cm and about 3 μm (i.e., 0.01 THz to 100 THz). As an added benefit, terahertz radiation can be used to analyze a sample mixture that has been heated sufficiently to excite one or more of the vibrational and rotational levels of the molecules. Such an analysis is possible at such elevated temperatures, at least in part because 1 THz is equivalent to 0.004 eV photon energy. Thus, the use of terahertz radiation can offer additional flexibility for oilfield application including downhole sample analysis.

Various embodiments of the present invention provide an apparatus and method for determining a composition of a fluid sample including a mixture of one or more of oil, water, and gas using a source of electromagnetic radiation operating within the terahertz spectrum.

In one aspect, the invention relates to a sample analyzer for analyzing a sample gas, liquid, or combination of a gas and a liquid. The device includes a sample chamber having a fluid communication port configured to receive the sample. The device also includes a filter in fluid communication with the fluid communication port, such that the sample received by the sample chamber is filtered by the filter. A terahertz radiation detector is provided in electromagnetic communication with the sample. The terahertz detector provides a detected output signal indicative of the terahertz electromagnetic radiation detected from the sample. In some embodiments, the device also includes a terahertz source illuminating the sample, the terahertz detector detecting a portion of the terahertz source illumination as modified by the sample. The detected portion of the spectrum of terahertz radiation can be processed to analyze the composition of the sample.

In another aspect, the invention relates to a borehole apparatus for analyzing a composition of a fluid sample obtained from a formation, for which the fluid sample includes at least one of water, oil, and gas. The borehole apparatus includes at least one sample chamber within the borehole for containing a fluid sample. The at least one sample chamber includes a first window portion substantially transparent to terahertz radiation. The apparatus also includes a terahertz detector in electromagnetic communication with the fluid sample, the terahertz detector generating an output signal indicative of the terahertz electromagnetic radiation detected from the fluid sample. In some embodiments, the device also includes a terahertz source illuminating the fluid sample, the terahertz detector detecting a portion of the terahertz source illumination as modified by the fluid sample. The detected portion of the spectrum of terahertz radiation can be processed to analyze the composition of the fluid sample.

In yet another aspect, the invention relates to a process for analyzing the composition of a fluid sample obtained from a formation, the fluid comprising at least one of water, oil, and gas. A fluid sample is first obtained within a borehole and directed into at least one sample chamber. At least a portion of a spectrum of terahertz radiation is directed from the fluid sample into the at least one sample chamber. The detected portion of the spectrum of terahertz radiation is processed to analyze the composition of the fluid sample.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

In order to provide additional flexibility to fluid/gas identification analysis and thus provide higher quality reservoir evaluations, terahertz radiation is applied in oilfield applications. One example of such an application includes downhole fluid/gas composition analyses, using gas/liquid chromatography and other composition analysis systems.

Performing compositional analysis using terahertz radiation sources and detectors provides additional flexibility by avoiding absorption peak overlaying experienced by optical and near-IR approaches. Terahertz spectroscopy covers in the electromagnetic spectrum the region from at least 0.01 to about 100 terahertz (from 0.3 to 3000 $cm^{-1}$), when converted to other units, 1 terahertz corresponds to a 300 µm free-space wavelength, which is also equivalent to 33.33 $cm^{-1}$ (wave numbers), 0.004 eV photon energy, or about ⅙ of the average thermal energy of a degree of freedom at 300 K. Terahertz frequencies are suitable for probing low energy light-matter interactions, such as rotational transitions in molecules, phonons in solids, plasma dynamics, electronic fine structures in atoms, thermal imaging of cold sources, and vibration-rotation tunneling behavior in weakly bonded clusters.

Terahertz radiation can be applied to spectrographic analysis to obtain spectral signatures of a sample material within the terahertz frequency band. The spectral signatures include one or more of absorption, emission, and reflection response versus frequency of a sample. Different samples, yield different spectral responses within this frequency band, referred to as a terahertz signature for the respective sample.

Terahertz signatures resulting from molecular rotations, and vibrations are compound/element specific allowing for selective, safe, marker-free identification of molecules and molecular aggregates in a mixture. Beneficially, the terahertz signatures can be used as a detector for liquid chromatography including gas-liquid mixtures; gas chromatography; and other compositional analysis systems using terahertz emission radiation. In some embodiments, the terahertz analysis systems use one or more of the terahertz excitation and absorption processes. Alternatively or in addition, terahertz radiation can be used to distinguish between samples having different water content, because terahertz radiation is absorbed by water.

Multiple different techniques can be used to perform terahertz analysis. Some of the more important techniques can be arranged into two broad categories: (i) frequency-domain analysis and (ii) time-domain analysis. One or more of these analyses may include a transform from time domain, or delay domain to frequency domain using any one of a number of standard transforms. Such transforms include Fourier transforms, fast-Fourier transforms (FFT), and wavelet transforms.

A Fourier transform technique can be used to analyze a sample placed in an optical interferometer system. The optical interferometer system combines light from multiple sources in an optical instrument to accomplish various precise measurements. Such techniques are well know to those skilled in the art. A Michelson-Morley interferometer is an example of one such optical interferometer. The interferometer has at least two different optical paths, or arms extending from the same optical source. The sample is illuminated with a broadband thermal source such as an arc lamp. The path length of one of the interferometer arms is varied, or scanned, representing a variable optical delay line. A direct detector, such as a bolometer can be used to detect an interference signal resulting from interactions between the two different paths of light from the same source (one through the sample and the other through the variable-length delay line). The Fourier transform of the detected signal can be calculated in real time (e.g., FFT, or during post processing) using standard processing techniques to yield a power spectral density of the sample. The resulting spectrum provides information about the sample mixture composition within terahertz range.

Measurements having a much higher resolution may be made using a narrowband system with a tunable terahertz device. The tunable device includes at least one of a terahertz source and a terahertz detector. In some embodiments, the tunable device includes a terahertz source and a terahertz detector, with at least one of the terahertz source and detector being tunable. In these systems, the wavelength of the source and/or detector is tuned across a desired bandwidth (e.g., terahertz band) allowing a sample's response (e.g., absorptivity, emissivity, and reflectivity) to be measured directly. Both Fourier transform analysis and narrowband analysis can be used in passive systems for monitoring thermal-emission lines of molecules. In this case a terahertz generator is not needed, only a detector, since the sample itself generates emissions within the terahertz spectrum.

Terahertz time-domain analysis using short pulses of broadband terahertz radiation is one example of a time-domain approach. The short pulses can be generated using currently available ultra-fast laser pulses. Pulsewidths are currently available of around 100 femtoseconds or even less. At least one exemplary device capable of providing such a short pulse is a Ti-Sapphire laser.

Preferably, the transmitted terahertz electric field is measured coherently to provide a time-resolved phase information, with a greater sensitivity. Such detection can be accomplished using a photoconductive detector. The terahertz beam passing through the sample chamber interacts with an analyzable sample disposed within the chamber through photon excitation and de-excitation. Interaction of the incident radiation with the sample leads to a corresponding time delay in a response pulse arriving at the detector. By varying the time at which a sample pulse is received and comparing at the detector the response pulse with the delayed sample pulse, a pulse profile within the time domain can be obtained. The time domain spectral results can be recorded and processed by a Fourier or wavelet analysis to obtain a corresponding frequency domain spectrum.

Figure 1:
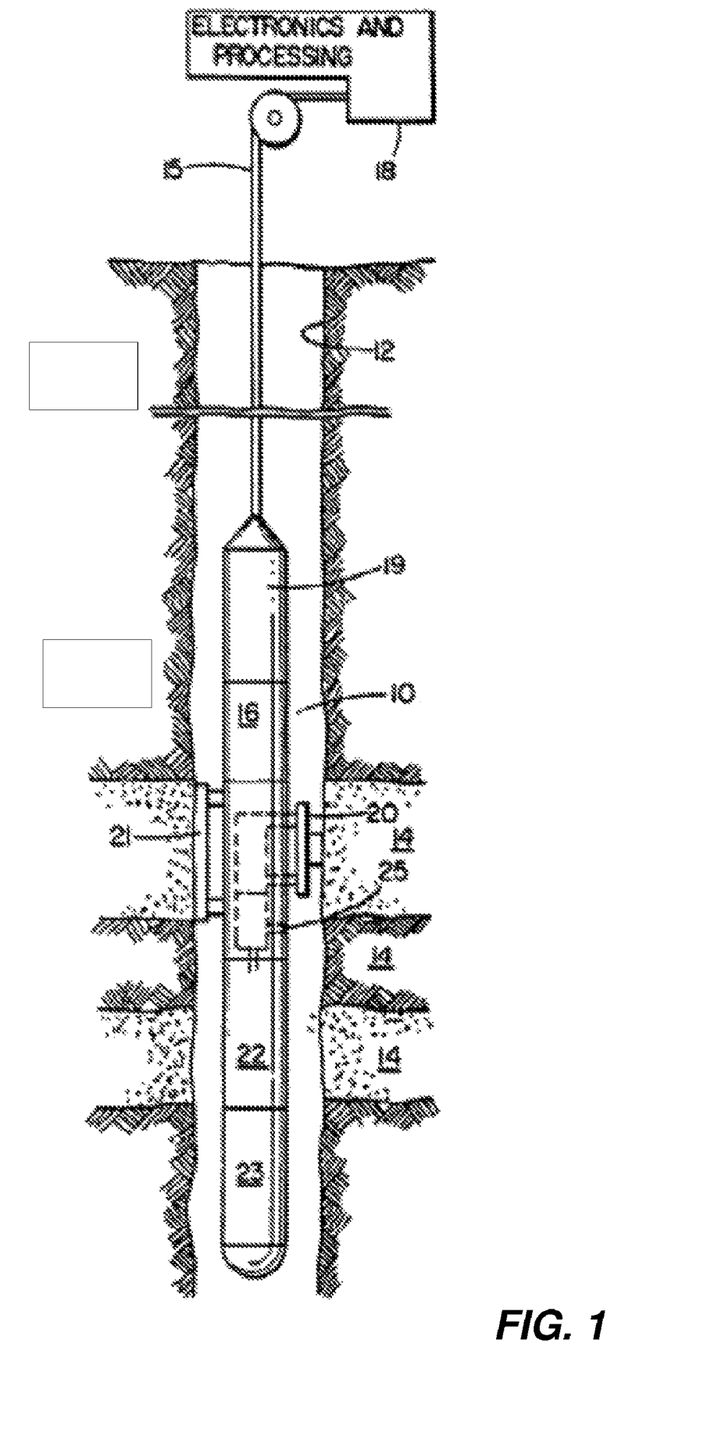
FIG. 1 shows a cutaway view of an exemplary borehole including an elevation view of an embodiment of the present invention configured for borehole applications.

FIG. 1 illustrates an exemplary configuration for performing fluid/gas composition analyses using a downhole analyzer. A borehole logging tool 10 is provided for testing earth formations and analyzing the composition of fluids from the formation 14. In some embodiments, the logging tool 10 is replaced with a drilling tool including a logging capability for logging information while drilling. Either of the logging tool 10 and drilling tool can include a memory capability or mode for storing information obtained while the device is downhole. The borehole tool 10 is suspended in a borehole 12 from the lower end of a cable 15 that is spooled in the usual fashion on a suitable winch (not shown) on the formation surface. More generally, the cable 15 can include any other type of umbilical, drill string, or other type of conveyance methods. On the surface, the cable 15 is connected to an electrical control system 18. The tool 10 includes an elongated body 19 that encloses the downhole portion of the tool control system 16. The elongated body 19 also carries a selectively extendible fluid admitting assembly 20 and a selectively extendible tool anchoring member 21 that is respectively arranged on opposite sides of the body 19, as shown. The fluid admitting assembly 20 is equipped for selectively sealing off or isolating selected portions of the wall of the borehole 12, such that the pressure or fluid communication with the adjacent earth formation is established.

Also included with the tool 10 are a fluid analysis module 25, through which the obtained fluid flows. The fluid may thereafter be expelled through a port (not shown) or it may be sent to one or more fluid collecting chambers 22 and 23. Control of the fluid admitting assembly, the fluid analysis section, and the flow path to the collecting chambers can be maintained by the electrical control systems 16 and 18. Additional details of methods and apparatus for obtaining formation fluid samples may be had by reference to U.S. Pat. No. 5,166,747 to Schroeder et al. and assigned to the assignee herein.

Figure 2:
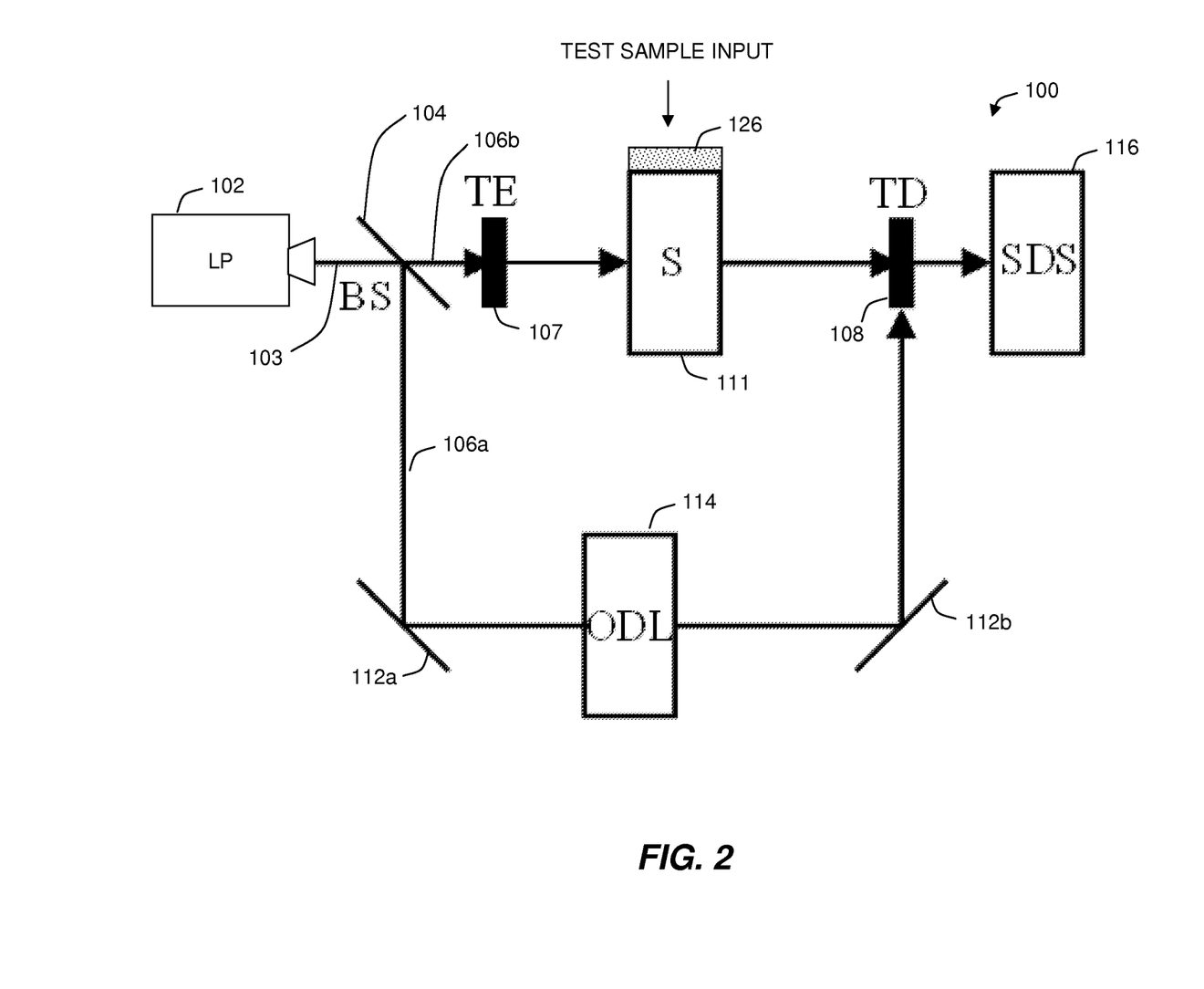
FIG. 2 shows a schematic block diagram of one embodiment of a terahertz mixture analyzer.

To provide composition analysis of a fluid, a gas, and combinations of a fluid and a gas, a sample from the formation is retrieved into the tool 10 and passes through a composition analysis module 25, where at least one cell with a representative mixture, is exposed to terahertz radiation. A schematic diagram of an exemplary THz sample analysis module is shown in FIG. 2. The analysis module 100 includes a THz radiation source that includes a short-pulse laser 102 and a terahertz emitter 107. A fast laser pump 102 induces terahertz emission in a device, such as an Auston switch 107. A portion of the fast pulse is split off using a first beam splitter 104 and directed to a sample chamber 111 through a separate path. The sample chamber 111 optionally includes a filter 126 in fluid communication with an input port to filter a sample before it enters the sample chamber 111. The analysis module 100 also includes optical propagation system having components selected from the group consisting of: mirrors 112a, 112b; lenses; prisms; filters; and optical delay lines 114. In some embodiments, the analysis module includes more than one sample chambers. Such multi-chamber devices can be used to perform analyses on different samples obtained by different levels of filtering. Alternatively or in addition, the multi-chamber devices can be used to perform different measurements and analyses using combinations of one or more of the techniques described herein. In some embodiments, the techniques described herein can be combined with other measurement and analysis techniques previously available to oilfield applications.

In the exemplary embodiment, the terahertz radiation source 102 emits a directed beam of terahertz radiation 103 that is split into at least two separate beams 106a, 106b using a beam splitter 104. A first one of the split beams 106a is routed to the detector 108 in a direct manner, through the propagation system including a first mirror 112a, an optical delay line 114, and a second mirror 112b, and not through the sample chamber 111. The optical delay system through which the direct beam 106a is routed is provided to compensate for a delay of the second beam 106b encountered during propagation through sample cell. The optical delay system is also used to evaluate initial terahertz beam.

Figure 3:
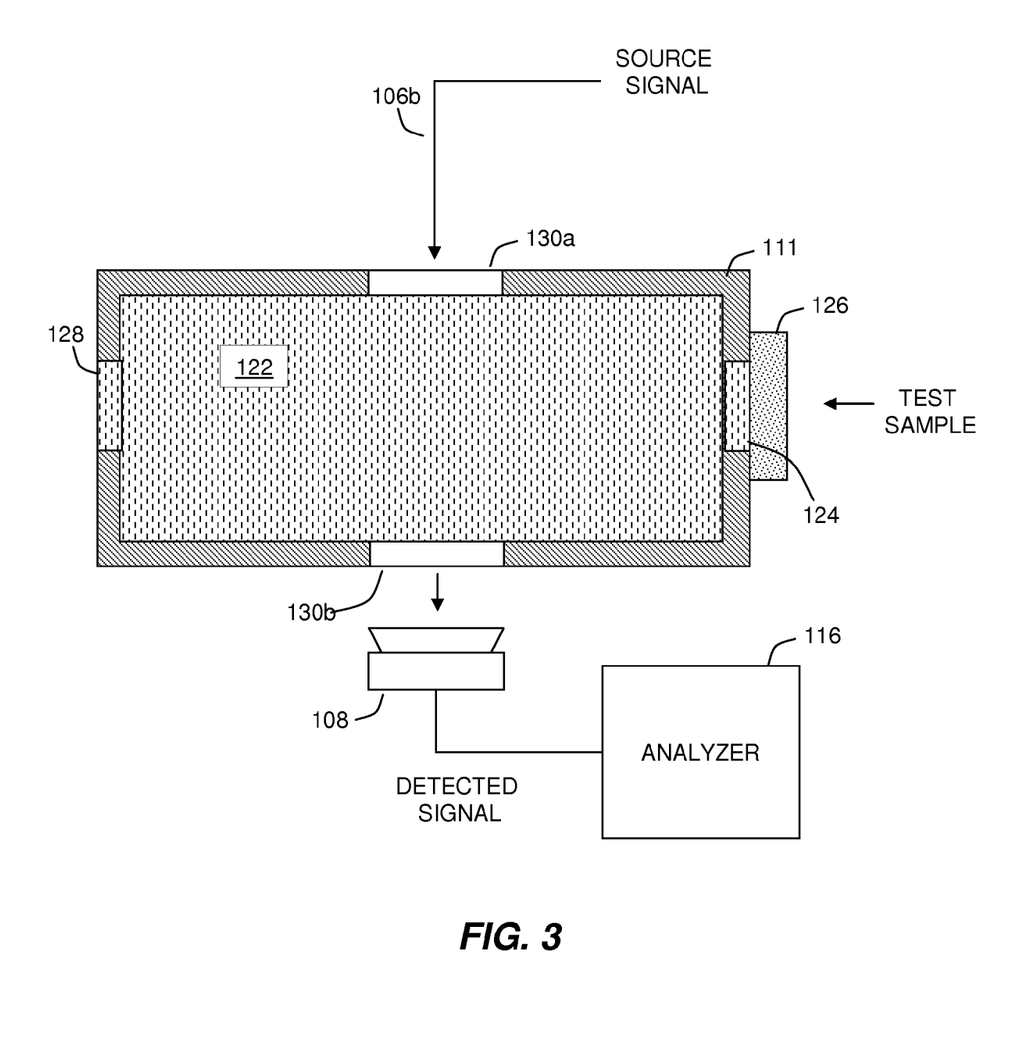
FIG. 3 shows cross-sectional diagram of one embodiment of a sample chamber shown in the terahertz mixture analyzer of FIG. 2.

A second one of the split beams 106b is directed through the test sample chamber 111. The test sample chamber 111 defines a cavity including a test sample of material to be analyzed. The second beam 106b passing through the sample chamber 111 interacts with a sample mixture 122 (FIG. 3). The fraction of terahertz radiation absorbed per unit path length in a sample mixture depends on the chemical composition (i.e., the identity and the concentration, or amount, of the constituent compounds) of the sample and the wavelength of the terahertz radiation. Thus, there is a selective absorption in the terahertz wavelength region that can be used for composition analyses. The optical delay system is used to sweep the delay between the detected source and sample laser pulses. In this manner, the electric field waveform can be measured for increasing delays, such that the time waveform can be reconstructed. Application of a time to frequency transformation yields a spectral response. This technique can be referred to generally as time-domain spectroscopy.

The terahertz radiation sources 107 can include a quantum cascade laser (in this case TE is positioned instead of element 102). Such devices are known for their high optical output power, substantial tunability, and room temperature operation, that together make it well suited for spectroscopic applications like the remote sensing of environmental gases.

In general, the principal components of terahertz analysis system can be grouped into at least five broad categories. These categories include: (i) sources that emit terahertz radiation; (ii) propagating components that deliver terahertz signals to a sample that needs to be evaluated; (iii) detectors, that detect a terahertz signal; (iv) signal analyzers; and (v) software that computes detector signals and control communications between system and user.

Continuous wave sources of narrow-band THz radiation are generally used for spectroscopy with very high frequency resolution. Power levels of a few milliwatts are sufficient for many spectroscopy and imaging applications. Such power levels have been achieved in continuous wave (CW) sources in portions of the THz electromagnetic spectrum. One class of narrowband CW terahertz sources use microwave generation followed by frequency multiplication. These are commercially available, compact, all-solid-state devices. Tuning bandwidths are typically 5-10% for highest power devices, up to 40% with some sacrifice of power. Power ranges from 30 milliwatts near 0.2 THz to about 1 microwatt near 1.6 THz. An exemplary device is the 1.26-1.31 THz solid state source, commercially available from Virginia Diodes, Inc., of Charlottesville, Va.

Another class of narrowband CW sources includes backward wave oscillators. Output power levels vary from about 100 milliwatts near 0.1 THz to about 1 milliwatt at 1.2 THz. Current designs output multimode beams. Photocurrent-based photomixers can also be used with a tuning range from about 0.1 to about 3 THz in a single device. Power levels are typically below 1 microwatt at frequencies above 1 THz. Still other devices use photomixers based on nonlinear optical crystals. These devices provide milliwatts of narrow-band THz power using high-power pulsed pump lasers. The conversion efficiency is ultimately limited by ratio of THz to visible photon energy.

$CO_2$ laser-pumped molecular gas lasers are spot tunable (that is, the frequency cannot be continuously varied), but provide substantial power levels of up to 1 Watt at 2.5 THz. This class of sources is generally referred to as optically pumped terahertz lasers (OPTL). One example is Model No. SIFIR-50 pumped laser terahertz source commercially available from Coherent, Inc. of Santa Clara, Calif. Another class of laser sources includes THz quantum cascade lasers. These are very new, and very rapid progress is being made in their development. Quantum cascade lasers in which inter-sub band or inter-miniband transitions in layered semiconductor heterostructures are used to generate light in the THz region of the spectrum. At present, THz quantum cascade lasers preferably are cooled to temperatures below those achievable with thermoelectric coolers. Output powers are typically a few milliwatts. At least one example of a broadband, pulsed terahertz source is the Auston switch.

An Auston switch refers to a broadband, short-pulse source of electromagnetic radiation within the terahertz frequency band. The device essentially consists of a split electrodes fabricated on a semiconductor substrate to create a switch. The electrodes can be in the form of a simple dipole antenna. Suitable semiconductor substrates include low-temperature gallium arsenide (LT-GaAs), semi-insulating gallium arsenide (SI-GaAs), and other semiconductors including InP and ZnTe. A direct-current (DC) bias (e.g., 40 Volts) is applied across the antenna and an ultra-short pump-laser pulse is focused in the gap of the split antenna. Preferably, the pulse width is less than about 100 femtoseconds. The laser pulse in combination with the DC bias, allows electrons to effectively "jump" the gap, resulting in a current within the antenna that produces a terahertz electromagnetic wave.

The low output power of THz sources coupled with the relatively high levels of thermal background radiation in this spectral range has generally necessitated highly sensitive detection methods. For broadband detection, direct detectors based on thermal absorption are commonly used. Most of these generally require cooling to reduce thermal background. The most common systems are helium-cooled silicon, germanium and InSb bolometers. Pyroelectric infrared detectors may also be used at THz frequencies. Superconductor research has yielded extremely sensitive bolometers based on the change of state of a superconductor such as niobium. Interferometric techniques may be used to extract spectral information using direct detectors.

Terahertz radiation detectors 108 include bolometers; pyroelectric detectors; photoacoustic cells; and Auston switches, without the bias (i.e., a dipole antenna). The detector 108 detect a first component of terahertz radiation transmitted through the test sample chamber 111 and a second component of terahertz radiation from the same source, transmitted through a delay line. The detector 108 provides a detector signal output signal responsive to the detected terahertz radiation.

In applications requiring very high spectral resolution of the sensor, heterodyne sensors are preferred. In these systems, a local oscillator source is mixed with the received signal at the THz frequency. The downshifted signal is then amplified and measured. At room temperature semiconductor structures may be used.

For pulsed THz detection in THz-TDS systems, coherent detectors are required. The two most common methods are based on photoconductive sampling (for example based on Auston switch principle THz detector described in more detail below) and free-space electro-optic sampling, both of which rely on ultra fast laser sources. One skilled in the art will readily recognize that numerous alternative sources and detectors exits which may be used in practicing the present invention. The following description of the present invention in view of an Auston switch is solely for illustrative purposes and clarity. One skilled in the art will recognize that various detectors such as, but not limited to, bolometers, pyroelectric detectors, photoacoustic cells and electro-optic detectors may be utilized in practicing the present invention. Additionally, one skilled in the art will recognize that numerous alternative sources, including but not limited to, quantum cascade lasers, backward waves oscillators and OPTL may be utilized in practicing the present invention.

In view of the foregoing, the detector output signal is sent to a signal detection system 116, in which further processing of the test sample can be performed. For example, the signal detector system 116 can be used to compute absorption coefficients for the different wavelengths. Absorption coefficients of the sample can be compared to these from existing database and different components of the analyzable mixture can be identified.

In more detail, an embodiment of the test chamber 111 is shown in cross section in FIG. 3. The chamber 111 includes an inlet port 124 through which a sample 122 enters the chamber 111. A filter 126 is optionally provided in fluid communication with the inlet port 124 to filter the sample in a predetermined manner. The test chamber 111 also includes a first window 130a that is substantially transparent to terahertz radiation. The window 130a is placed along an optical path between the source 102 (FIG. 1) and the chamber 111. Terahertz radiation enters the interior of the chamber 111 through the first window 130a, illuminating the sample 122 dispensed therein.

The chamber 111 includes a second window 130b also substantially transparent to terahertz radiation, through which a portion of the terahertz radiation exits the chamber 111. In some embodiments, the windows 130a, 130b can be made of a plastic that is transparent to terahertz radiation. In some embodiments, the first and second windows 130a, 130b are aligned, such that incident terahertz radiation entering the first window 130a traverses the sample 122 within the chamber 111 and exits the second window 130b. The windows 130a, 130b are in fluid-tight communication with the chamber 111 to retain a fluid sample 122 within the chamber 111. The detector 108 can be optically aligned with the pair of windows 130a, 130b to capture terahertz radiation emanating from the chamber 111. In some embodiments, the chamber also includes an exit port 128 through which a sample 122 may exit the chamber 111. In this manner, the test sample 122 can include a flow.

Figure 4:
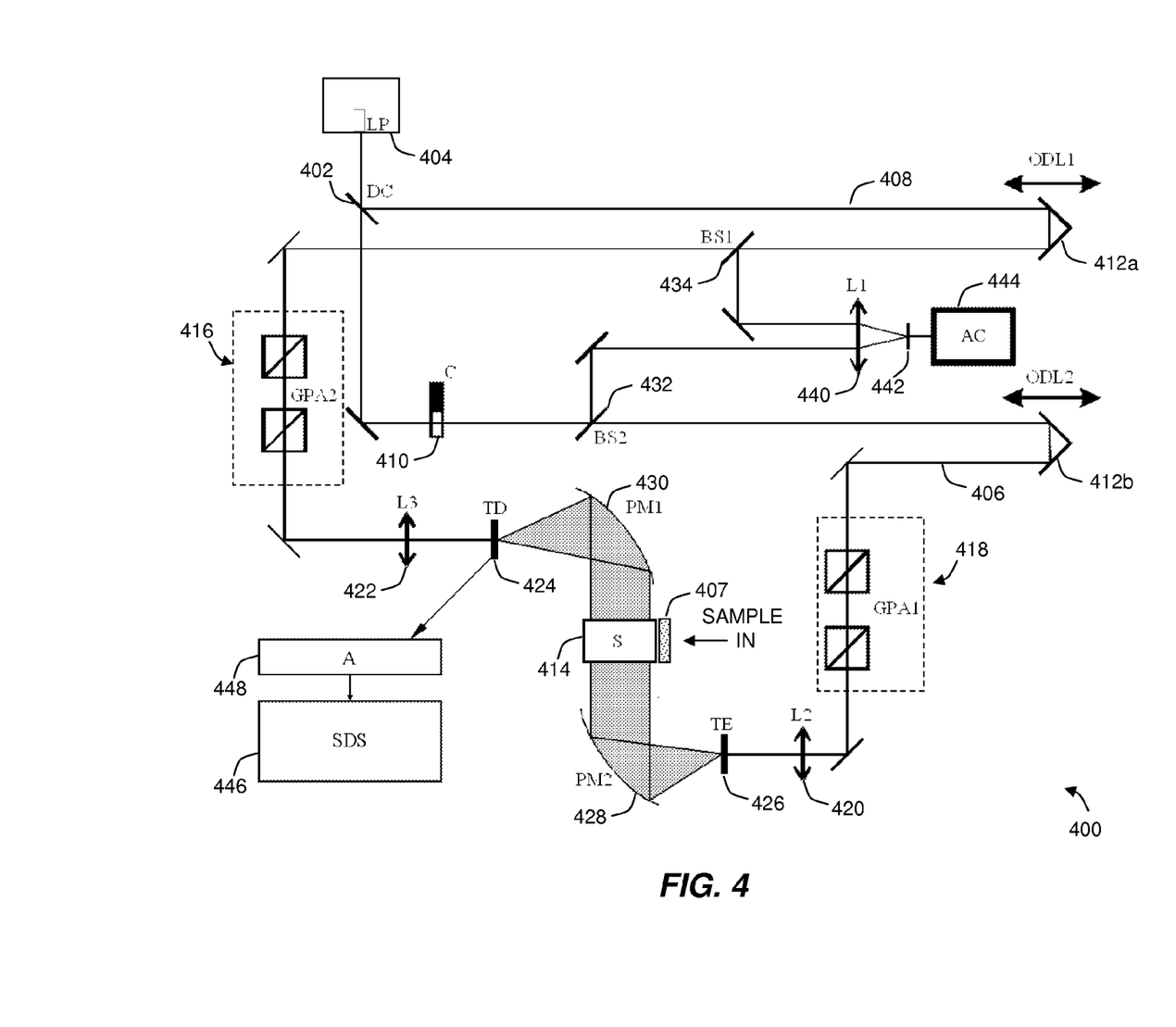
FIG. 4 shows a schematic block diagram of another embodiment of a terahertz mixture analyzer including a multipath sample chamber for performing liquid or gas chromatography.

An alternative class of terahertz spectrometer 400 also useful in making a composition analysis of downhole fluid/gas shown in the schematic diagram of FIG. 4. A dividing cube 402 divides a laser pulse from femto-second laser 404 (e.g., Ti:Sapphire) (that laser pulse can be delivered from the logging unit on surface by means of electromagnetic conduit, such as a fiber optic cable) into two parts. One part passes through the dividing cube 402 and is directed to terahertz emitter arm 406. A second part of the laser pulse is reflecting within the dividing cube 402 and directed into a terahertz detector arm 408. An optical chopper 410 is specially introduced in the TE arm 406 to periodically interrupt the terahertz beam in that arm. Such regular interruptions can be used to detect synchronically a terahertz detection signal. For example, the chopper 410 only allows radiation to pass through during a specific time frame. This interrupted signal can be used to lock an amplifier to specific frequency.

A first optical delay line (ODL1) includes a first angled mirror 412*a* and is used to obtain a time profile of the terahertz pulse. A second optical delay line (ODL2) includes a second angled mirror 412*b* and is used to compensate for a delay related to propagation through the sample cell 414 and to obtain a time profile. Each of a first and second Glan prism systems 416, 418 includes two or more Glan prisms (GP1 and GP2) together providing a respective power attenuator in each of the TE arm 406 and the TD arm 408. Each of the individual prisms GP1, GP2 used within the Glan prism systems 416, 418 can include a Glan-Taylor prism, a Glan-laser prism, or a combination of both prisms. Generally, Glan-laser prisms are known for their high power capacity in handling laser emissions. Using these power attenuators 416, 418 the amplitude of the laser radiation can be changed without changing its plane of polarization.

Two lenses 420, 422 are provided: a first lens 420 focusing laser radiation onto terahertz emitter (e.g., Auston switch); and a second lens 422 focusing laser radiation onto the terahertz detector 424 (e.g., Auston switch, electro-optic detector).

The terahertz emitter 426 is placed at a focus of a first parabolic mirror 428, directing emitted terahertz radiation toward the parabolic mirror 428. This creates a parallel terahertz beam reflected from the mirror 428, which can be directed along an optical path toward a first side of a sample cell 414. A second parabolic mirror 430 is aligned along an opposite side of the sample cell 414 and in alignment with the parallel beam from the first parabolic mirror 428. The second parabolic mirror 430 focuses terahertz energy received from the sample cell 414 onto the terahertz detector 424 placed at its focus.

Two beam splitters 432, 434 are also provided. The first beam splitter 434 is placed in the detector arm after angled reflector 412*a* on the first optical delay line 408 and the second beam splitter 432 is placed before the second optical delay line 406. The beams from both beam splitters 432, 434 are focused by a third lens 440 onto a nonlinear crystal 442. One example of such a crystal 442 is a Potassium DiDeuterium Phosphate crystal (KDP), noted for its non-linear optical properties, used in optical modulators, and in non-linear optics such as second harmonic generation. An output from the nonlinear crystal 442 is detected and as a result autocorrelation function of laser pulse is recorded in correlator 444.

First, the first optical delay line 408 is preferably positioned to yield a maximal signal from the correlator 444. The second optical delay line 406 is subsequently adjusted, such that the terahertz pulse directed through sample cell 414 and optical pulse directed to the terahertz detector 424 through the second arm match in time. Once established, the first optical delay line 406 time profile of terahertz pulse is recorded in signal detection system 446 after amplification in amplifier 448.

To perform downhole chromatography compositional analysis of gaseous mixtures, a sample is first retrieved from the formation into the tool 10 as described above in reference to FIG. 1. The retrieved sample passes through a composition analysis module 25 including at least one of the gas chromatography or liquid chromatography systems described herein, in which a chromatographic separation of the sample occurs.

To provide additional flexibility of this chromatography system, an additional detector using terahertz radiation is installed in combination (e.g., series, parallel) with a one or several common chromatography detectors like thermal conductivity detector (TCD), flame ionization detector, photo ionization detector. A TCD is an example of a common detector used in chromatography. Beneficially, a TCD detector is non-destructive, such that it can be operated in-series with another detector. The other detector can be any of the terahertz detectors described herein or another gas chromatography detector. Should a destructive detector be utilized, the terahertz detector should be positioned in a location before the destructive detector. For example, the TCD can be connected before a terahertz detector to provide complementary detection of the same eluents. To avoid excessive peak-broadening, the connection between these detectors can be made with a capillary tube. The outlet of such a capillary tube can be connected to the terahertz detector sample cell.

Figure 5:
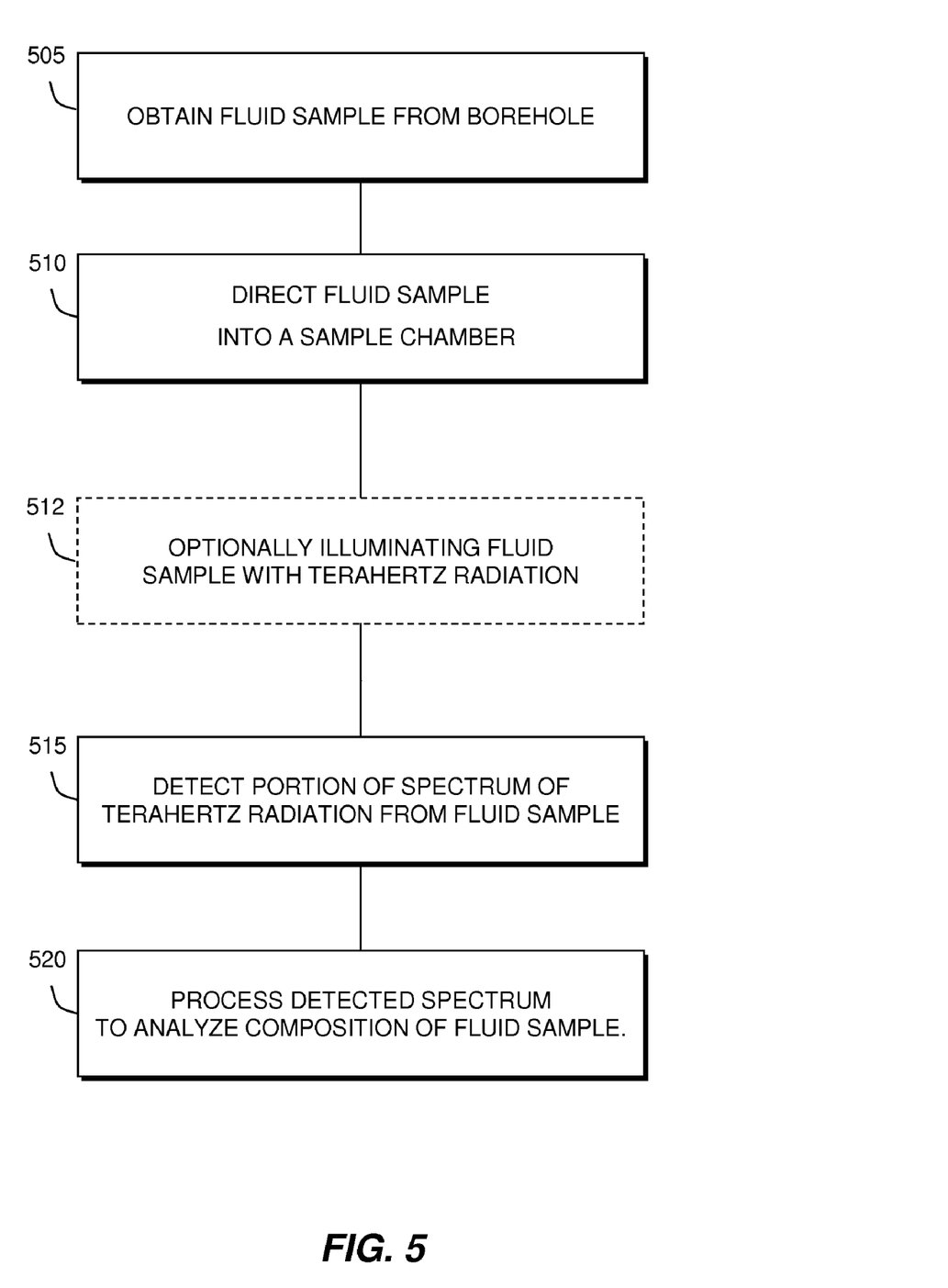
FIG. 5 shows a functional block diagram of a process for analyzing a mixture in accordance with the principles of the present invention.

An exemplary process for analyzing the composition of a fluid sample obtained from a formation is shown in FIG. 5. A fluid sample is first obtained from within a borehole (505) and directed into at least one sample chamber (510). At least a portion of a spectrum of terahertz radiation is directed from the fluid sample into the at least one sample chamber (515), in some cases through the filter system that allow to selectively remove at least one of oil, water, gas component from the reservoir mixture. The detected portion of the spectrum of terahertz radiation is processed to analyze the composition of the fluid sample (520). In some embodiments, the detector is passive, detecting electromagnetic emissions from the sample occurring within the terahertz waveband. In some embodiments, the fluid sample is illuminated (512) by a source of electromagnetic radiation, such as a terahertz beam. Such illumination contributes to at least a portion of the spectrum of terahertz radiation directed from the fluid sample.

Figure 6:
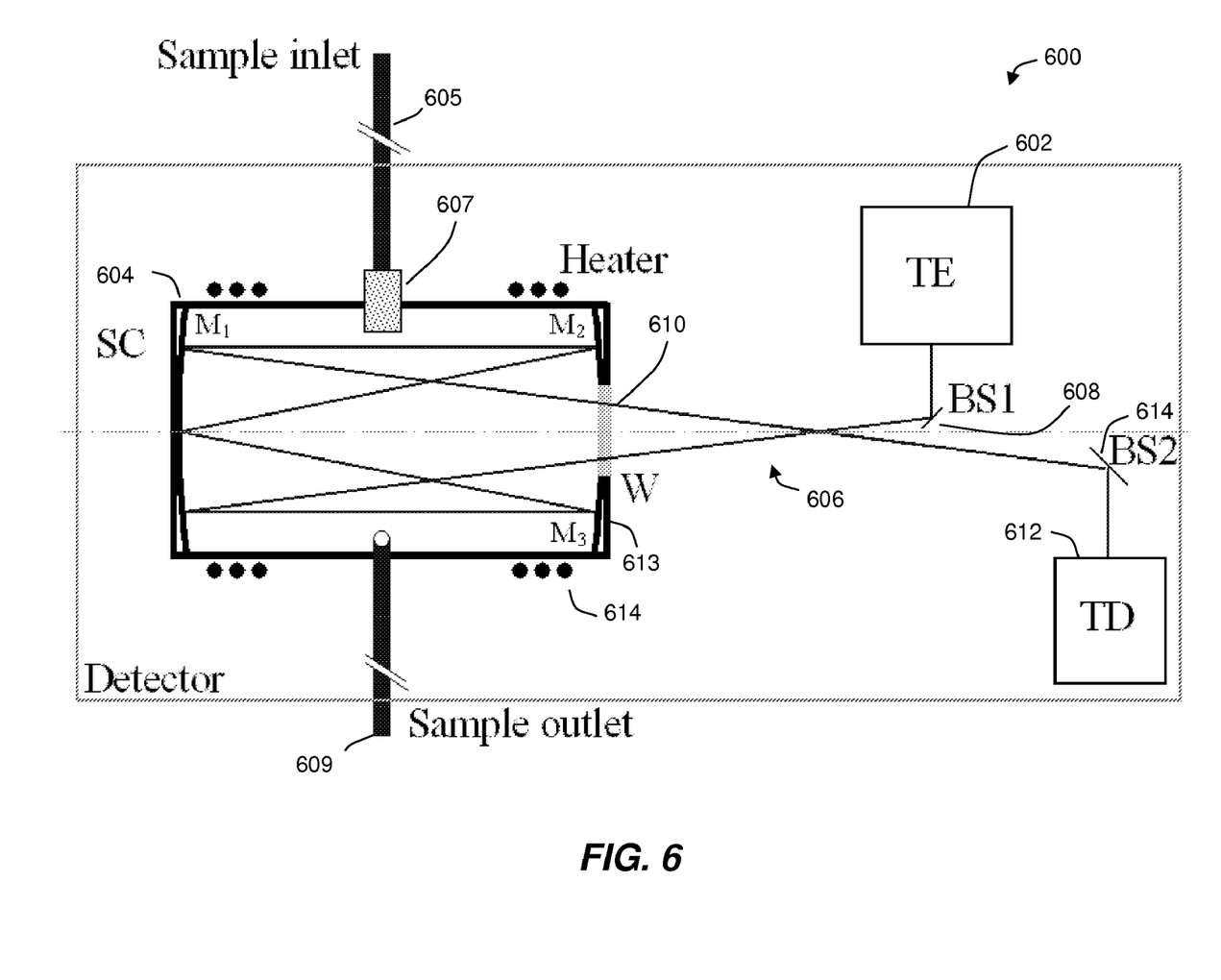
FIG. 6 shows a schematic block diagram of an embodiment of a terahertz mixture analyzer including a sample chamber absorption terahertz spectroscopy of a gas sample.

An alternative embodiment of a detector for chromatography and other composition analysis applications is shown in FIG. 6. The chromatography device 600 includes a terahertz emitter 602 providing a source of terahertz radiation. In some embodiments, the terahertz emitter 602 includes a quantum cascade laser and a dipole antennas (e.g., Auston switch). The terahertz radiation is routed from the emitter 602 to a sample chamber 604 through a propagation system 606. Similar to optical systems, the propagation system 606 can include one or more of: lenses, filters, sample cells; and beam splitters.

During compositional analysis, it is advantageous to minimize experimental error introduced by a sample chamber due to its imperfections, or even its mere presence. Such corrections can be accomplished by separately characterizing spectral contributions of an empty sample chamber. In some embodiments, the "empty" chamber may include a compound, such as an inert gas during the separate characterization process. Once obtained, chamber contributions can be effectively removed from spectral results obtained from a sample within the sample chamber.

In an exemplary process for removing contributions of the sample chamber, the spectrum of empty sample chamber is separately recorded as a first spectrum. This may be accomplished as an initial step before a test sample is measured, or subsequently during post processing. The spectrum of sample chamber and reservoir mixture is obtained as a second spectrum. This step can be accomplished using any of the techniques described herein. The first spectrum can be subtracted from the second spectrum to obtain spectrum of reservoir mixture unaffected by sample chamber contamination or degradation.

In particular, a first beam splitter 608 is placed in the optical path between the terahertz source 602 and the sample chamber 604. An incident beam from the terahertz source is split into two different beams. A first one of the beams is directed directly through a window 610 provided on a side of the sample chamber 604 adjacent to the beam splitter 608. The window 610 can be made using a material that is transparent to terahertz radiation, such as a plastic. Preferably, the window material is substantially impervious to the sample environment, such that its properties are not degraded when operating in its intended environment. One such class of materials includes polyetheretherketones (PEEK), also referred to as polyketones. PEEK is an engineered thermoplastic known for its extraordinary mechanical properties and also for exhibiting good chemical resistance in many environments, including aromatic hydrocarbons and oils.

Another part of the split beam can be used to analyze the initial terahertz beam to correct for environmental drift effects in the emitter and detector equipment and circuitry. This second beam (not shown) can be directed to a monitoring detector configured to monitor such performance factors.

In some embodiments, the window 610 defines an aperture that is smaller than an adjacent side 613 of the sample chamber 604. When the incident beam enters the window 610 along an optical path at an angle of incidence, as shown, the incident beam traverses a length of the sample chamber 604 more than twice as a result of multiple internal specular reflections within the chamber 604. Ultimately, the multiply reflected terahertz radiation beam exits the same window 610 along a different optical path, or trajectory than the incident beam. The exit beam is routed to a detector 612 that is adapted to detect terahertz radiation. As shown, the beam that interacted with the sample mixture finally exits the sample chamber 604 through the window 610 and is directed to the detector 612 through a second beam splitter 614. Preferably when split, a significant part of the beam (e.g., more than 50%) is directed to the terahertz detector 612, while a lesser remaining part can be used for feedback monitoring of the terahertz emitter 602.

A fraction of terahertz radiation absorbed in an analyzable mixture is proportional to the beam path length. Thus, sensitivity of the device 600 can be improved by increasing the path length of the terahertz beam within the sample chamber 604. A longer path length corresponds to a greater terahertz radiation absorption. One solution would be to provide an elongated test chamber. A preferred solution, however, is represented by the exemplary device 600 causing the same incident beam to traverse the sample more than twice through multiple internal reflections. Such a shortened device 604 is better suited to the size limitations encountered bore hole testing. In some embodiments, actual reflective surfaces, such as specular mirrors are strategically located along the interior of the sample chamber. The exemplary system 600 includes three mirrors (M1, M2, M3) that reflect the beam as shown. In some embodiments, the sample chamber includes a resonant cavity.

In some embodiments, a heater 614 is added to the sample chamber. The heater 614 can be an electrical heater and is adapted to provide temperature control of the sample chamber 604 to within a specific range, such as ±0.05 degrees-C. range. The heater 614 is primarily provided to avoid condensation of components. The heater 614 can also be useful in establishing and maintaining a substantially uniform temperature field. The heater 614 can be formed using one or more of common electrical filaments and other suitable thin film structure.

The fraction of terahertz radiation absorbed per unit path length in a sample mixture depends on the chemical composition of the sample (i.e., the identity and the concentration, or amount, of the constituent compounds) and the wavelength of the terahertz radiation. Thus, there is an absorption in the terahertz wavelength that can be used for composition analyses.

The terahertz detector 612 detects transmitted terahertz radiation and sends a detected signal to a signal detection system (not shown). Absorption coefficients for the different wavelengths can be computed in the signal detection system. Absorption coefficients of the sample can be compared to these from an existing database and different components of the analyzable mixture can be identified. Such comparisons can be accomplished automatically using a processor to read analysis results and compare them to a database of known stored results. Some exemplary devices that can be used for terahertz detectors include: bolometers; pyroelectric detectors; and photoacoustic cells.

Figure 7:
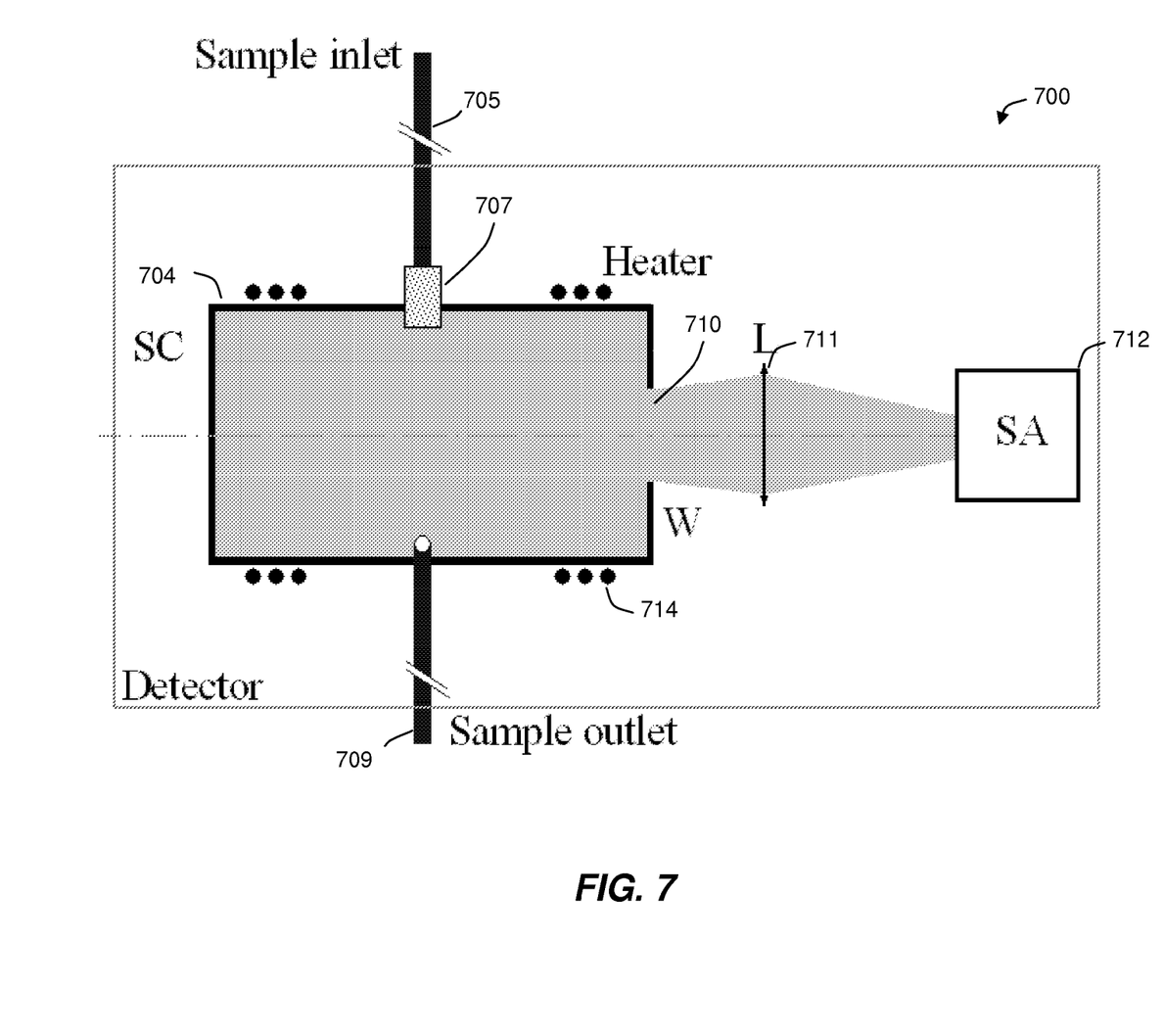
FIG. 7 shows a schematic block diagram of yet another embodiment of a terahertz mixture analyzer including a sample chamber adapted for emission terahertz spectroscopy of a gas sample.

An alternative approach uses terahertz emission spectroscopy without the need for a separate terahertz source. Such a device 700 is shown in FIG. 7 and can be used effectively in the case of high concentration of analyzable mixture. In this case, after gas chromosome analysis, the heated mixture is passed through a capillary column 705 coming into the sample chamber 704. In some embodiments, the sample flows through a filter 707 before entering the chamber 704. Similar to the previous example, the sample chamber 704 includes a window 710 that is transparent to terahertz radiation. Through this window 710 part of terahertz radiation resulting from emissions from the heated sample emanates out through the window 710 directed from interior of the sample chamber 704. A focusing lens 711 can be provided external to the sample chamber 704 and along an optical path between the window 710 and a sample analyzer 712. The lens 711 focuses emitted radiation onto the sample analyzer 712. In some embodiments, the sample analyzer 712 is a combination of a terahertz detector and a signal detection system. In some embodiments, a heater 714 is added to the detector to avoid condensation of the analyzable mixture within the sample chamber. Preferably, an electric heater 714 is added to an exterior surface of the sample chamber and configured to provide temperature control of the sample chamber to within desired tolerance, such as ±0.05 degrees C. range.

Figure 8:
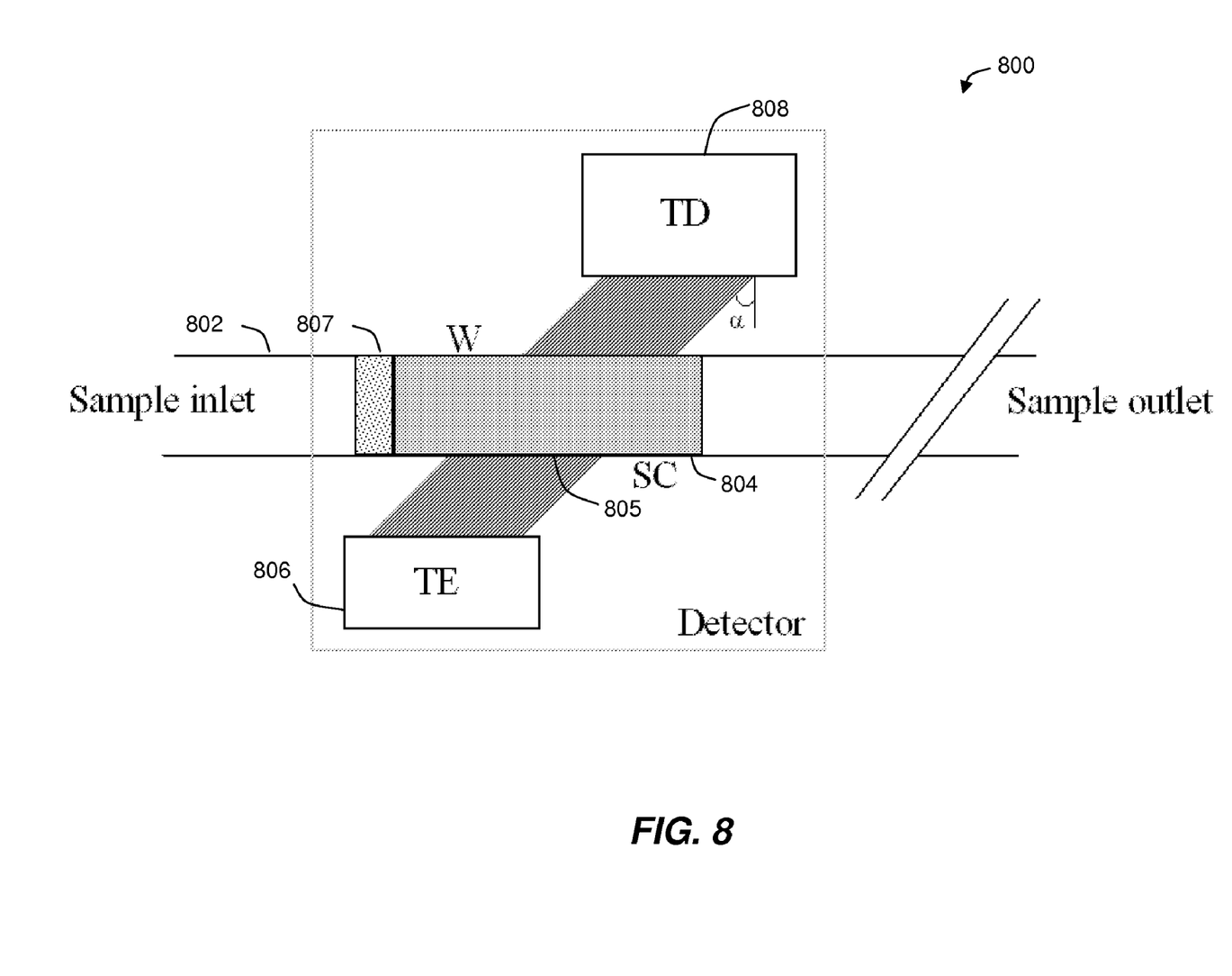
FIG. 8 shows a schematic block diagram of one embodiment of a terahertz detector adapted for performing liquid chromatography using absorption terahertz spectroscopy.

For liquid chromatography systems in which the concentration of an analyzable mixture is higher than in a gas chromatography system, another type of absorption detector can be used. With a high concentration of analyzable mixture, it is possible to perform analyses through a capillary column. An exemplary liquid chromatography system 800 is shown in FIG. 8. The system includes a column 802 supporting flow of a sample liquid. In some embodiments a filter 807 is included to selectively filter the flow. The device 800 includes a window 805 substantially transparent to terahertz radiation. In some embodiments, the window 805 is formed by part of the column 802 made from a suitable window material (e.g., PEEK).

A terahertz source 806 provides terahertz radiation that can be routed from any of the terahertz emitters described herein, through a propagation system that can include one or more of lenses, sample cells, filters, and a beam splitter (not shown). A first portion of the split terahertz source beam is routed through a direct channel to a terahertz detector 808 without passing through the sample cell 804. The direct channel (not shown) includes an optical delay system to compensate for delay associated with a second portion of the split terahertz beam propagating through the sample chamber 804. The delayed sample from the terahertz source 806 can be used to evaluate the initial terahertz beam.

Another part of the beam interacts with the sample chamber 804, which in this case, is part of the column 802. The beam passes through the sample chamber 804, within which it interacts with the analyzable mixture. Through photon-molecular interaction processes, a part of the beam (depending on the chemical composition and concentration) is absorbed within the sample mixture within the sample chamber 804.

Thus, the sample mixture within the sample chamber 804 attenuates the beam before reaches the terahertz detector 808. The terahertz detector 808 detects the terahertz radiation transmitted through the sample chamber (the transmitted terahertz radiation approximating the incident radiation, less reflected radiation, less absorbed radiation) and sends a signal to a signal detection system (not shown), in which absorption coefficients for the different wavelengths can be computed.

To increase the path length of the terahertz beam through the sample chamber 804, and to achieve benefits related to increased path length described above, the beam is directed toward the sample chamber 804 at an angle α. Longer path lengths can be achieved for non-perpendicular directed beams. A relationship of the effective path length ($l_{eff}$) to angle of incidence (α) is:

$$l_{eff} = \frac{D_{column}}{\cos(\alpha)}, \qquad (1)$$

where $D_{column}$ is the column diameter.

Figure 9:
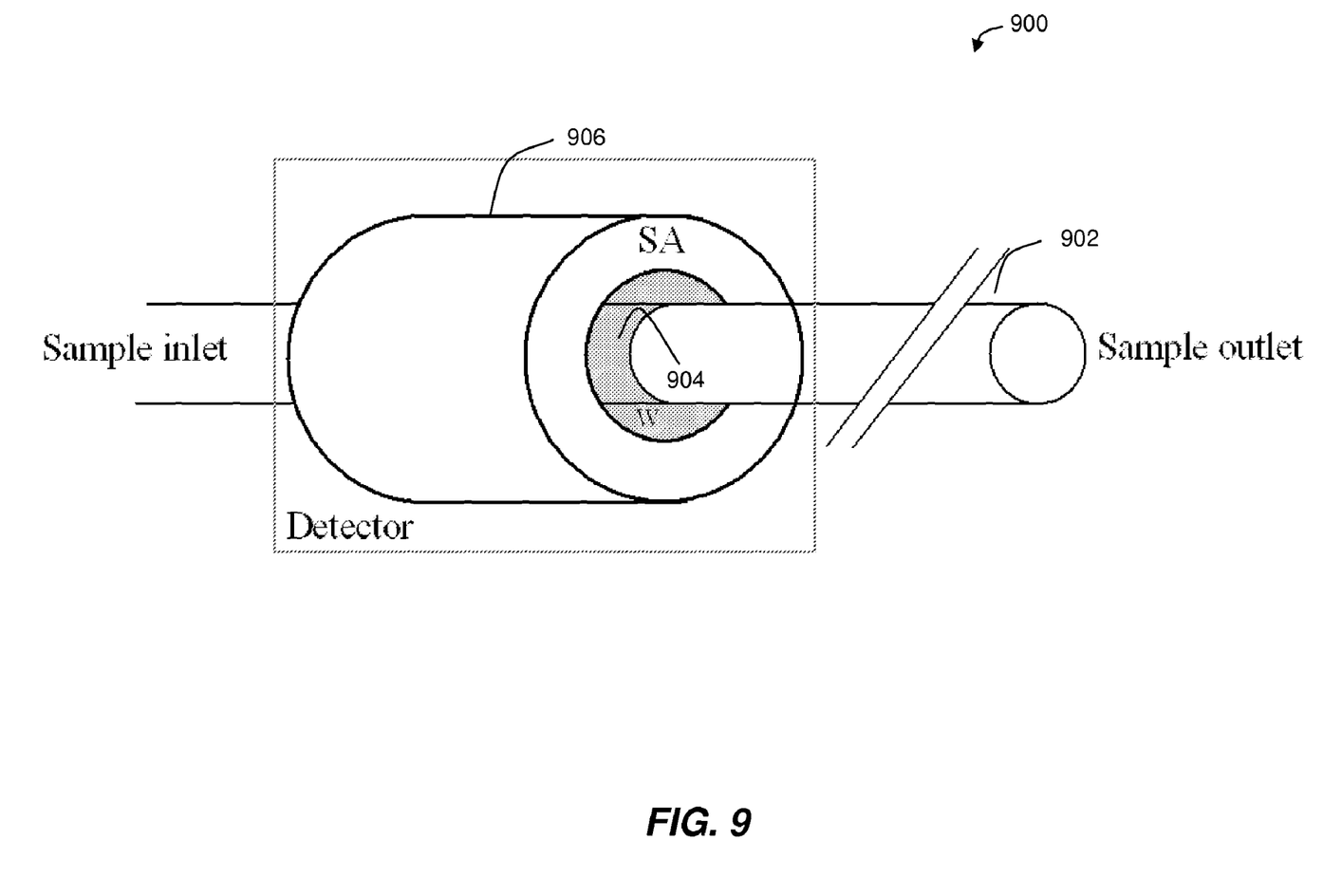
FIG. 9 shows a schematic block diagram of an alternative embodiment of a terahertz detector for performing liquid chromatography using emission terahertz spectroscopy.

Referring to FIG. 9, an alternative embodiment is shown including a detector configured for emission spectroscopy of high concentrations of analyzable mixtures. The system 900 includes a column 902 supporting flow of a sample liquid. In some embodiments a filter is included (not shown) to selectively filter the flow. The device 900 includes a window 904 substantially transparent to terahertz radiation. In some embodiments, the window 904 is formed by part of the column 902 made from a suitable window material (e.g., PEEK). A detector signal analyzer combination is formed in an annular fashion, coaxially aligned with the column 902 and centered about the window 904. This configuration allows terahertz radiation from the heated mixture to reach the sample analyzer 906. The sample analyzer 906 includes a detector and a signal detection system. Such a configuration allows for almost all of the emitted radiation to reach the sample analyzer to facilitate detection of lower concentrations of the analyzable mixture.

In some embodiments, one or more of the terahertz sources, when used with a respective window, can be aligned at a preferred angle, corresponding to the optical path and a normal to the window surface. In some instances, the preferred angle of incidence corresponds to the Brewster angle, such that a terahertz radiation of a preferred polarization is not reflected from the surface. The Brewster angle is a well-known function of the indexes of refraction of the respective media on either side of the window boundary (e.g., glass-air). In other instances, the preferred angle of incidence corresponds to a critical angle, such that a terahertz radiation incident upon one side of the window is subject to total internal reflection. Determination of the critical angle is achieved using a well-known function of the indexes of refraction of the respective media on either side of the window boundary (e.g., glass-air).

Any of the sample analysis chambers described herein can be purged. In some embodiments, the entire sample analysis chamber is purged using a suitable gas, such as nitrogen, helium, or any other noble gas. Alternatively, only those regions through which a terahertz beam passes are purged with a similar gas.

Referring again to FIG. 1, the analysis module 25 includes at least one of the measurement systems described herein to perform a respective one of the analyses described herein. In some embodiments, substantially all of the equipment to perform the measurement and analysis are provided within the logging tool 10. Control and/or results can be communicated between the logging tool 10 and the surface electrical control systems 18 using the cable. Alternatively or in addition, control and/or results can be recorded in the tool memory or send to surface acquisition system by other means of communication. In this instance, the cable may include one or more of metal conductors, such as shielded twisted pair and coaxial cables, and fiber optic cables.

In some embodiments, the source of terahertz radiation is placed on the surface and delivered to a sample analyzer in the logging tool 10 using a means of electromagnetic communication, such as low-loss coaxial cable, or optical fiber. Alternatively or in addition, a source of ultra-short laser pulse is placed on the surface and delivered to a sample analyzer in the logging tool 10 using a means of electromagnetic communication, such as an optical fiber.

While this invention has been particularly shown and described with references to preferred embodiments thereof, it will be understood by those skilled in the art that various changes in form and details may be made therein without departing from the scope of the invention encompassed by the appended claims.

What is claimed is:

1. A sample analyzer for analyzing a sample, comprising:
    a sample chamber having a fluid communication port configured to receive the sample;
    a filter in fluid communication with the fluid communication port, the sample received by the sample chamber being filtered by the filter;
    a terahertz radiation detector in electromagnetic communication with the sample located downhole in a borehole environment, the terahertz radiation detector generates from the sample a detected output signal indicative of electromagnetic radiation;
    wherein the detected output signal is within the spectral region from about 0.01 terahertz to about 20 terahertz; and
    a processor receiving the detected output signal from the terahertz radiation detector and analyzing the sample using the detected output signal, wherein the processor analyzes the sample in case of a time-domain spectral and a corresponding frequency domain spectrum, whereby the time domain spectral results are recorded and processed by the analysis to obtain the corresponding frequency domain spectrum.

2. The sample analyzer of claim 1, wherein the filter comprises at least one molecular membrane configured to selectively removes at least one of water, oil, and gas, for a fluid sample comprising more than one of water, oil, and gas.

3. The sample analyzer of claim 1, further comprising a terahertz source in electromagnetic communication with the sample, the emitting radiation having a first wavelength.

4. The sample analyzer of claim 3, wherein the terahertz source can vary for the emitted radiation, one or more of: frequency, amplitude, and phase of the terahertz radiation.

5. The sample analyzer of claim 3, wherein the terahertz source emits radiation at more than one wavelength, the terahertz radiation detector providing a detected output signal indicative of the detected terahertz electromagnetic radiation from the sample.

6. The sample analyzer of claim 3, wherein the terahertz source emits a temporal pulse of terahertz radiation or continuous radiation.

7. The sample analyzer of claim 3, wherein a wavelength of the terahertz radiation is selectable.

8. The sample analyzer of claim 3, wherein the terahertz source comprises an Auston switch.

9. The sample analyzer of claim 1, wherein the processor analyzes the sample using a Fourier transform or wavelet analysis in case of one of a time-domain terahertz spectroscopic mixture analysis, corresponding frequency domain spectrum, or both.

10. The sample analyzer of claim 1, comprising a second sample chamber having a fluid communication port configured to receive a second sample, the terahertz radiation detector in electromagnetic communication with the second sample and providing a detected output signal indicative of the detected terahertz electromagnetic radiation from the sample.

11. The sample analyzer of claim 1, wherein the sample chamber comprises at least one window partially transparent to terahertz radiation, a normal to the at least one window being aligned with incident terahertz radiation at a Brewster angle.

12. The sample analyzer of claim 1, wherein the sample chamber comprises at least one window partially transparent to terahertz radiation, a normal to the at least one window being aligned with incident terahertz radiation beyond a critical angle, such that the incident terahertz radiation is subjected to full internal reflection.

13. The sample analyzer of claim 1, wherein the terahertz radiation detector comprises an Auston switch.

14. A borehole apparatus for analyzing a composition of a fluid sample obtained from a formation, the fluid sample comprising at least one of water, oil, and gas, the apparatus comprising:
at least one sample chamber for containing the fluid sample within the borehole, the at least one sample chamber including a first window portion that is substantially transparent to terahertz radiation;
a terahertz detector in electromagnetic communication with the fluid sample located downhole in a borehole environment, the terahertz detector generating an output signal responsive to at least a portion of the spectrum of terahertz radiation from the fluid sample between about 0.01 terahertz and about 20 terahertz; and
a processor receiving the detected output signal from the terahertz radiation detector and analyzing the fluid sample using the detected output signal, wherein the processor analyzes the fluid sample in case of a time-domain spectral and a corresponding frequency domain spectrum, whereby the time domain spectral results are recorded and processed by the analysis to obtain the corresponding frequency domain spectrum.

15. The borehole apparatus of claim 14, further comprising a terahertz radiation source in electromagnetic communication with the fluid for emitting terahertz radiation, the terahertz detector detecting at least a portion of the emitted terahertz radiation in addition to the spectrum of terahertz radiation received from the fluid sample in the at least one reservoir.

16. The borehole apparatus of claim 14, wherein the at least one sample chamber further includes a second window portion that is also substantially transparent to terahertz radiation, the terahertz radiation emitted by the terahertz radiation source being in electromagnetic communication with the fluid sample through the second window portion.

17. The borehole apparatus of claim 14, wherein the at least one sample chamber further includes at least one mirror system to provide multiple reflection of terahertz radiation within the sample chamber thereby increasing a length of photon-molecular interaction between the terahertz radiation and fluid sample.

18. The borehole apparatus of claim 14, further comprising a filter in fluid communication with the at least one sample chamber, the fluid sample entering the at least one sample chamber through the filter.

19. The borehole apparatus of claim 18, wherein the filter comprises at least one molecular membrane configured to selectively removes at least one of water, oil, and gas, for a fluid sample comprising more than one of water, oil, and gas.

20. The borehole apparatus of claim 14, further comprising a source of terahertz radiation placed on a surface and delivered to the sample chamber through an electromagnetic conduit.

21. The borehole apparatus of claim 20, wherein the source of terahertz radiation comprises an Auston switch.

22. The borehole apparatus of claim 14, further comprising a source of ultra-short laser pulses placed on a surface and delivered to the sample chamber through an electromagnetic conduit.

23. The borehole apparatus of claim 14, wherein the terahertz detector comprises an Auston switch.

24. A method for analyzing the composition of a fluid sample obtained from a formation, the fluid comprising at least one of water, oil, and gas, the method comprising:
obtaining the fluid sample within a borehole;
directing the fluid sample into at least one sample chamber;
detecting from the fluid sample within the at least one sample chamber at least a portion of a spectrum of terahertz radiation between about 0.01 terahertz and about 20 terahertz located downhole in a borehole environment; and
using a process for processing the detected portion of the spectrum of terahertz radiation to analyze the composition of the fluid sample, wherein the processor analyzes the fluid sample in case of a time-domain spectral and a corresponding frequency domain spectrum, whereby the time domain spectral results are recorded and processed by the analysis to obtain the corresponding frequency domain spectrum.

25. The method of claim 24, wherein detecting comprises detecting at least a portion a spectrum of terahertz radiation from the fluid sample disposed within the at least one sample chamber, through a first window portion of the at least one reservoir substantially transparent to terahertz radiation.

26. The method of claim 24, further comprising illuminating the fluid sample in the at least one sample chamber with terahertz radiation.

27. The method of claim 26, wherein the wavelength of the illuminating terahertz radiation is between about 3 cm and about 3 µm.

28. The method of claim 26, wherein the step of illuminating the fluid sample comprises varying the wavelength of the terahertz radiation during illumination.

29. An analyzer for analyzing a sample while in a subterranean environment, comprising:
- a sample chamber having a fluid communication port configured to receive the sample while in the subterranean environment;
- a filter in fluid communication with the fluid communication port, the sample received by the sample chamber being filtered by the filter;
- a terahertz radiation detector in electromagnetic communication with the sample located downhole in a borehole environment of the subterranean environment, the terahertz radiation detector generates from the sample a detected output signal indicative of electromagnetic radiation;
- wherein the detected output signal is within the spectral region from about 0.01 terahertz to about 20 terahertz; and
- a processor receiving the detected output signal from the terahertz radiation detector and analyzing the sample using the detected output signal, wherein the processor analyzes the sample in case of a time-domain spectral and a corresponding frequency domain spectrum, whereby the time domain spectral results are recorded and processed by the analysis to obtain the corresponding frequency domain spectrum.

* * * * *